United States Patent
Meijer et al.

(10) Patent No.: US 6,316,456 B1
(45) Date of Patent: Nov. 13, 2001

(54) PURINE DERIVATIVES HAVING, IN PARTICULAR, ANTIPROLIFERATIVE PROPERTIES, AND THEIR BIOLOGICAL USES

(75) Inventors: Laurent Meijer, Roscoff; Emile Bisagni, Orsay; Michel Legraverend, Antony, all of (FR)

(73) Assignees: Centre National de la Recherche Scientifique, Davis Cedex (FR); Institute of Experimental Botany, Lỳsolaje (CZ); a part interest ( * ) Notice: Subject to any disclaimer, the term of this patent is extended or adjusted under 35 U.S.C. 154(b) by 0 days.

(21) Appl. No.: 09/077,470

(22) PCT Filed: Nov. 29, 1996

(86) PCT No.: PCT/FR96/01905

§ 371 Date: Aug. 31, 1998

§ 102(e) Date: Aug. 31, 1998

(87) PCT Pub. No.: WO97/20842

PCT Pub. Date: Jun. 12, 1997

(30) Foreign Application Priority Data

Dec. 1, 1995 (FR) .................................................. 95 14237

(51) Int. Cl.[7] .................. C07D 473/16; A61K 31/52; A61P 35/00
(52) U.S. Cl. ..................... 514/261; 544/265; 544/277
(58) Field of Search .................. 544/277, 265; 514/261, 266

(56) References Cited

U.S. PATENT DOCUMENTS

| | | | |
|---|---|---|---|
| 2,691,654 | * 10/1954 | Hitchings | 544/277 |
| 2,830,053 | * 4/1958 | Hitchings | 544/264 |
| 2,844,577 | * 7/1958 | Acker | 544/277 |
| 2,966,488 | * 12/1960 | Shive | 544/277 |
| 3,213,095 | * 10/1965 | Bambury | 544/277 |
| 3,862,189 | * 1/1975 | Schwender | 544/277 |
| 3,930,005 | * 12/1975 | Wojnar | 544/277 |
| 3,989,833 | * 11/1976 | Jonas | 544/277 |
| 4,086,347 | * 4/1978 | Friebe | 544/277 |
| 4,100,286 | * 7/1978 | Regnier | 544/277 |
| 4,189,485 | * 2/1980 | Matsuno | 544/277 |
| 4,199,574 | * 4/1980 | Schaeffer | 544/277 |
| 4,212,866 | * 7/1980 | Friebe | 544/277 |
| 5,110,818 | * 5/1992 | Allgeier | 544/277 |
| 5,117,830 | * 6/1992 | McAfee | 128/654 |
| 5,866,702 | * 2/1999 | Mackman | 544/277 |

FOREIGN PATENT DOCUMENTS

390112 * 10/1990 (EP).

OTHER PUBLICATIONS

Pelech, Neurobiology of Ageing 16(3) 247, 1995.*
Vesely et al., "Inhibition of Cyclin–Dependent Kinases By Purine Analogues", *European Journal of Biochemistry*, vol. 24, No. 2, Sep., 1994, pp. 771–786.
Parker Chemical Abstracts, vol. 104, No. 19, (May 12, 1986), Abstrct No. 164159a, pp. 274.
Hocart Chemical Abstracts, vol. 115, No. 23, (Dec. 9, 1991), Abstract No. 252157f, p. 471.
Tao, Chemical Abstracts, vol. 117, No. 5, (Apr. 3, 1992), Abstract No. 44644b, pp. 534.

* cited by examiner

Primary Examiner—Mark L. Berch
(74) Attorney, Agent, or Firm—Foley & Lardner (57) ABSTRACT

This invention provides 2-, 6, and 9-substituted purine derivatives having, in particular, antiproliferative properties, and suitable for use as pharmaceutical compositions and herbicidal compositions. Also provided are pharmaceutical compositions and herbicidal compositions comprising the 2-, 6, and 9-substituted purine derivatives, and methods of treatment using the 2-, 6, and 9-substituted purine derivatives.

4 Claims, 7 Drawing Sheets

PURINE DERIVATIVES HAVING, IN PARTICULAR, ANTIPROLIFERATIVE PROPERTIES, AND THEIR BIOLOGICAL USES

This is a national stage application of PCT/FR96/01905, filed on Nov. 29, 1996, which claims priority of French application 95/14237, filed Dec. 1, 1995.

The invention relates to new purine derivatives having anti-proliferative properties and to their biological uses.

It relates in particular to purine derivatives having an inhibiting effect with respect to cyclin-dependent kinase proteins, or cdk for short.

The study of the molecular mechanisms which control the cell cycle has demonstrated the regulatory role of cdk. These proteins are made up of at least two sub-units, a catalytic sub-unit (of which cdc2 is the prototype) and a regulatory sub-unit (cyclin). Eight cdk have been described, cdk1 (=cdc2), cdk2–cdk8.

With the exception of cdk3, for which no associated cyclin is known, the cdk are regulated by transitory combination with a member of the cyclin family: cyclin A (cdc2, cdk2), cyclin B1–B3 (cdc2), cyclin C (ckd8), cyclin D1–D3 (cdk2–cdk4–cdk5–cdk6), cyclin E (ckd2), cyclin H (cdk7).

Each of these complexes is involved in a phase of the cell cycle. The activity of the cdk is regulated by post-translational modification, by transitory combinations with other proteins and by modification of their intracellular location. Regulators of the cdk include activators (cyclins, cdk7/cyclin H, cdc25 phosphatases), the sub-units $p9^{CKS}$ and $p15^{cdk-BP}$ and the inhibitory proteins ($p16^{NK4A}$, $p15^{INK4B}$, $p21^{Cip1}$, p18, $p27^{Kip1}$).

In parallel with purely fundamental research into the regulatory mechanisms of cell division, the importance of dysregulations of cyclin-dependent kinases in the development of human tumours has been demonstrated by several studies. Over-expression of cyclins D and E in several tumours, over-expression of cdc2, the oncogenic properties of cyclins D and A, abnormal temporary expression of cyclin-dependent kinases and major dysregulation of protein inhibitors (mutations, deletions) have thus been found.

The regulators of the cell division cycle are the subject of a large number of clinical studies (use as indicating markers for treatment).

These results greatly encourage efforts for detailed comprehension of the regulatory mechanisms of the cell cycle. They also lead to the search, by screening for molecules which inhibit cyclin-dependent kinases.

Several kinase inhibitors have been described, such as butyrolactone, flavopiridol and 2-(2-hydroxyethylamino)-6-benzylamino-9-methylpurine, called olomoucine. Works relating to olomoucine are reported by Vesely et al. in the article carrying the reference (1) in the list of bibliographic references given at the end of the description.

This cdc2 inhibitor of high efficacy (its $IC_{50}$ is 7 $\mu$M) and high selectivity (more than 35 kinases have been tested) corresponds to the formula:

The works of the inventors in this field have led them to develop new molecules of particular interest which inhibit cdc2 in low doses, while maintaining the enzymatic specificity of olomoucine.

The object of the invention is therefore to provide new purine derivatives having, in particular, anti-proliferative properties.

The invention also relates to a process for obtaining these derivatives by synthesis, which enables them to be prepared on an industrial scale.

It also relates to their therapeutic use and their use as a herbicide.

The purine derivatives of the invention are characterized in that they correspond to the formula I.

in which
R2, R6 and R9, which are identical to or different from one another, represent a halogen atom or an R-NH-, R-NH-NH-, NH$_2$-R'-NH- or R-NH-R'-NH- radical, in which R represents a straight- or branched-chain, saturated or unsaturated alkyl radical, an aryl or cycloalkyl radical or a heterocyclic ring and R' represents a straight- or branched-chain, saturated or unsaturated alkylene group or an arylene or cycloalkylene group, R and R' each containing 1 to 8 carbon atoms and being substituted, where appropriate, by one or more -OH, halogen, amino or alkyl groups.

R2 can also represent a heterocyclic ring carrying, where appropriate, a straight- or branched-chain, saturated or unsaturated alkyl radical, an aryl or cycloaryl radical or a heterocyclic ring, optionally substituted by one or more -OH, halogen, amino or alkyl groups.

R9 can also represent a straight- or branched-chain, saturated or unsaturated alkyl radical or an aryl or cycloalkyl radical, R2 and R9 can also represent a hydrogen atom, with the exception of the derivatives in which the said substituents have, respectively, the following meanings:

R6 and R9 - a benzylamino and methyl group,
R2 and R6 - a hydroxyethylamino and benzylamino group,
R2, R6 and R9 - an amino, benzylamino and methyl, or chloro, amino and methyl, or chloro, benzylamino and methyl, or chloro, 3-hydroxybenzylamino and methyl, or chloro, 5-hydroxypentylamino and methyl, or 2-hydroxyethylamino, benzylamino and isopropyl, or 2-hydroxyethylamino, amino and methyl, or 2-hydroxyethylamino, isopentenyl and methyl, or 2-hydroxyethylamino, isopentenylamino and methyl, or 2-hydroxyethylamino, benzylamino and methyl, or 2-hydroxyethylamino, benzylamino and 2-hydroxyethyl, or 2-hydroxyethylamino, benzylamino and isopropyl, or 2-hydroxyethylamino, (3-hydroxybenzyl)amino and methyl, or 2-hydroxyethylamino, (3-hydroxybenzyl)amino and isopropyl, or 2-hydroxyisobutylamino, 6-benzylamino and methyl, or 2-hydroxyethylamino, isopentenylamino and isopropyl, or (2-hydroxyethyl)amino, (4-methoxybenzyl)amino and isopropylamino group.
and the purine derivatives of the invention are furthermore characterized in that they have an $IC_{50}$ less than or equal to about 5 μM for cdc2/cyclin B.

The abovementioned derivatives which are excluded from the invention are described in reference (1).

In general, the derivatives of the invention are kinase protein inhibitors of great interest.

Preferably, the halogen atom is chosen from chlorine, bromine or fluorine, the alkyl radical is chosen from the methyl, ethyl, propyl, isopropyl, butyl and isobutyl, pentyl, hexyl and heptyl radicals the alkylene radical is chosen from the methylene, ethylene, propylene, isopropylene, butylene, isobutylene, pentene or isopentene radicals, the aryl radical is a benzyl group, the cycloalkyl radical is a cyclohexyl group, the arylene radical is a benzylene group, the cycloalkylene radical is a cyclohexylene group and the heterocyclic ring is a nitrogen-containing and or oxygen-containing heterocyclic ring, such as an imidazole, an oxadiazole, a pyridine, a pyridazine or a pyrimidine, or also a pyrrolidine.

According to one embodiment of the invention, R2 is chosen from the radicals which are capable of bonding in a cdk2/ATP complex to a region of the bonding domain of ATP occupied by ribose. These are advantageously radicals chosen from a chlorine atom, and amino, methylamino, ethylamino, n-heptylamino, aminoethylamino, aminopropylamino, dimethyleminoethylamino, hydroxyethylamino, hydroxy-propylamino, hydroxyisobutylamino, hydroxypentylamino, dimethylhydrazino or hydroxymethylpropylamino. [(2R)-2-hydroxymethyl-pyrrolidin-1yl], N-benzyl-aminoethanol, (R,S)-amino-hexanol, (S)-amino-2-phenylethanol, (R)-amino-2-phenylethanol, (R)-amino-3-phenylpropanol, (R,S)-amino-pentanol, (R)-amino-propanol, (S)-amino-propanol and (R)-N-pyrrolidine-methanol radical.

Particularly preferred radicals contain a hydroxypropylamino radical as the group R2.

According to another embodiment of the invention, R6 is chosen from an amino, isopentenylamino, hydroxypentylamino, 4-hydroxy-3-methyl-trans-2-butenylamino, benzylamino, hydroxybenzylamino, hydroxyethylbenzylamino, cyclohexylmethylamino, isopentene, benzylamino or (3-iodo)-benzylamino group.

R6 preferably comprises a hydrophobic radical, such as benzyl, hydroxybenzyl or isopentenyl.

Preferably, R2 is chosen from the group consisting of [1-D,L-hydroxymethylpropylamino], [(2R)-2-hydroxymethyl-pyrrolidin-1-yl] and [(R)-N-pyrrolidine-methanol] and R6 is benzylamino.

According to yet another embodiment of the invention, the substituent R9 is chosen from a hydrogen atom and a methyl, isopropyl or hydroxyethyl radical.

R9 is advantageously a hydrophobic group, in particular the isopropyl group.

Preferred purine derivatives of the invention are chosen from the compounds in which R2, R6 and R9 are as indicated in the following table 1:

TABLE 1

| R2 | R6 | R9 | $IC_{50}$ μM cdc2/cyclin B |
|---|---|---|---|
| 3-hydroxypropylamino | benzylamino | isopropyl | 1 |
| 2-hydroxypropylamino | benzylamino | isopropyl | 0.9 |
| t-D,L-hydroxymethyl-propylamino | benzylamino | isopropyl | 0.65 |
| aminoehtylamino | benzylamino | isopropyl | 1 |
| 2-hydroxypropylamino | isopentenyl | isopropyl | 1.2 |
| 2-hydroxypropylamino | cyclohexyl-methylamino | methyl | 4 |
| chloro | isopentenyl-amino | isopropyl | 2.5 |
| (2R)-2-hydroxymethyl-pyrrolidin-l-yl | benzylamino | isopropyl-(9H) | 0.45 |
| N-benzylaminoethanol | benzylamino | isopropyl-(9H) | 2.5 |
| (R,S)-amino-hexanol | benzylamino | isopropyl-(9H) | 2.5 |
| (S)-amino-2-phenylethanol | benzylamino | isopropyl-(9H) | 4.3 |
| (R)-amino-2-phenylethanol | benzylamino | isopropyl-(9H) | 1 |
| (R)-amino-3-phenylethanol | benzylamino | isopropyl-(9H) | 2.7 |
| (R,S)-amino-pentanol | benzylamino | isopropyl-(9H) | 0.9 |
| (R)-amino-propanol | benzylamino | isopropyl-(9H) | 0.85 |
| (S)-amino-propanol | benzylamino | isopropyl-(9H) | 1 |
| (R)-N-pyrrolidine-methanol | (3-iodo)-benzylamino | isopropyl-(9H) | 0.45μM |
| (R)-N-pyrrolidine-methanol | benzylamino | cyclopentyl-(9H) | 0.7 |

The following derivatives are particularly preferred, that is to say: 2-1-D,L-hydroxymethylpropylamino)-6-benzylamino-9-isopropylpurine, non-crystalline 6-benzylamino-2-[(2R)-2-hydroxymethyl-pyrrolidin-1-yl]-9-isopropyl-(9H)-purine, 2-(R)-[6-benzylamino-9-isopropyl-(9H)-purin-2-yl]-amino-2-phenylethanol, 2-(R,S)-[6-benzylamino-9-isopropyl-(9H)-purin-2-yl]-amino-pentanol, 2-(R)-[6-benzylamino-9-isopropyl-(9H)-purin-2--yl]-amino-propanol, 2-(S)-[6-benzylamino-9-isopropyl-(9H)-purin-2-yl]-amino-propanol, 2-(R)-(-)-[6-(3-iodo)-benzylamino-9-isopropyl-(9H)-purin-2-yl]-N-pyrrolidine-methanol and 2-(R)-(-)-[6-benzylamino-9-cyclopentyl-(9H)-purin-2-yl]-N-pyrrolidine-methanol.

The invention also relates to the optical isomers and the racemic mixtures and, where appropriate, the geometric isomers of the derivatives defined above, in particular the R isomer of (2-[6-benzylamino-9-isopropyl-(9H)-purin-2-yl]-amino-2-phenylethanol and of 2-[6-benzylamino-9-isopropyl-(9H)-purin-2-yl]-amino-propanol.

The derivatives defined above are obtained by the conventional methods of organic synthesis. A starting purine derivative of which the substitutions allow introduction of the desired groups is used.

For example, using a 2-chloro-6-benzylamino derivative of purine, it is possible to introduce an alkyl group in position 9 by reaction with, for example, the corresponding alkyl halide.

Reaction with an aminoalcohol then allows introduction of an alkylhydroxyalkylamino group in position 2, in place of the chloro group.

According to an aspect of great interest, the derivatives of the invention have inhibitory properties on kinases of high selectivity. These inhibitory effects are reversible.

The cdk play a central role in the initiation, development and achievement of the events of the cell cycle, and the inhibitory molecules of cdk are capable of limiting undesirable cell proliferation, such as cancer, psoriasis and growth of fungi and parasites (animals, protists), and also of plants (herbicides), and of intervening in the regulation of neurodegenerative diseases, such as neuronal apoptosis and Alzheimer's disease.

The kinases which are more specifically sensitive to the inhibitory effects of these derivative are the cdc2, the cdk2 and cdk5.

Their inhibition is obtained with very low doses of purine derivatives.

An $IC_{50}$ with respect of cdc2 of less than 50 $\mu M$, and even than that of olomoucine (7 $\mu M$), which is regarded, however, as a potent inhibitor, has thus been observed most generally.

The invention particularly relates to purine derivatives having an $IC_{50}$ which does not exceed 5 $\mu M$, and especially 2-(1-D-L-hydroxymethylpropylamino)-6-benzylamino-9-isopropylpurine, also called roscovitine below, the $IC_{50}$ of which is 0.65 $\mu M$, non-crystalline 6-benzylamino-2-[(2R)-2-hydroxymethyl-pyrrolidin-1-yl]-9-isopropyl-(9H)-purine and 2-(R)-(-)-[6-(3-iodo)-benzylamino-9-isopropyl-(9H)-purin-2-yl]-N-pyrrolidine-methanol.

This derivative, which is an inhibitor of high efficacy and high selectivity with respect to the cdk, cdc2, cdk2 and cdk5, unexpectedly has in return effects on the kinases erk 1 and erk 2 similar to those of olomoucine. The selectivity is thus clearly superior with respect to cyclin-dependent kinases. This advantage, which is found with the other purine derivatives of the invention, allows elimination of interferences with the transduction routes of signals further upstream which involve the kinases erk 1 and erk 2 in several cell responses other than cell division.

The invention also relates to complexes of purine derivatives with the cdk, and especially to the crystallized form of the complex of cdk2 and roscovitine.

Studies carried out on the derivatives of the invention have shown, in addition to their specific inhibitory properties on kinases, cell effects and effects on apoptosis of great interest.

At a very low concentration (micromolar for roscovitine and a large number of derivatives), they are thus capable of inhibiting prophase/metaphase transition, as shown by experiments carried out on ovocytes of starfish and sea urchin embryos, which are reported in the examples.

On acellular Xenopus extracts, they are capable of inhibiting both the promoter factor of the M phase and DNA synthesis.

These cell effects are advantageously obtained at very low concentrations of derivatives.

It is known that various works relate to the relationships which exist between the cell cycle and apoptosis. Various routes lead to apoptosis of cells, some of which are dependent on kinases and others of which, in contrast, do not seem to require these enzymes. It has been demonstrated that apoptosis can be induced at the G1 and G2 stage, and that following damage to the DNA, some cells stop at the G1 stage and an apoptotic route dependent on p53 is thus induced.

In other situations, it seems that the cells stop at the G2/M stage, in response to damage caused to the DNA, and activation of an apoptotic p53-independent route is observed.

This route proves to be particularly important for treatment of tumours in which a loss of active p53 is found.

The benefit of having available, with the derivatives of the invention, means for stimulating a p53-independent apoptosis in cells which have stopped at the G2 stage by damage to the DNA with the aid of agents such as mitoxantrone or cis-platin is thus estimated.

The cdc2 inhibitors of the invention can thus increase the therapeutic effects of the anti-tumoral agents currently used.

As cdk5 inhibitors, the derivatives of the invention can also play a role in reducing abnormal hyperphosphorylation of tau observed during Alzheimer's disease.

To these various advantageous properties is added the benefit of absence of cytotoxicity of the derivatives of the invention.

The invention thus relates to the utilization of the properties of these derivatives, in particular their antimitotic and antineurodegenerative properties, for formulation of pharmaceutical compositions.

The pharmaceutical compositions of the invention are characterized in that they comprise an effective amount of at least one purine derivative as described above, in combination with an inert pharmaceutical vehicle.

The compositions of the invention are particularly suitable as antimitotic medicaments, in particular for chemotherapy of cancers, or also for treatment of psoriasis, parasitoses, such as those caused by protists or fungi, or Alzheimer's disease, or neuronal apoptosis.

These compositions comprise, where appropriate, active principles of other medicaments. There may be mentioned, in particular, their combination with antimitotic medicaments, such as those based on taxol, cis-platin, agents for intercalation of DNA and others.

The conditioning with respect to sale, in particular labelling and instructions for use, and advantageously packaging, are formulated as a function of the intended therapeutic use The pharmaceutical compositions of the invention can be administered in various forms, more specifically by an oral or injectable route.

For administration by the oral route, compressed tablets, pills, tablets, capsules and drops are used in particular. These compositions advantageously comprise 1 to 100 mg of active principle per dose unit, preferably 10 to 40 mg.

Other forms of administration include injectable solutions for the intravenous, subcutaneous or intramuscular route, formulated from sterile or sterilizable solutions. They can also be suspensions or emulsions.

These injectable forms comprise 1 to 50 mg of active principle, preferably 10 to 30 mg, per dose unit.

By way of indication, the dosage which can be used in man corresponds to the following doses for example, 10 to 50 mg/day are thus administered to the patient in one or more doses for treatment of tumours or to treat psoriasis parasitoses.

The invention also relates to herbicidal compositions comprising at least one purine derivative as defined above, optionally in combination with other phytopharmaceutical agents.

The invention also relates to biological reagents, the active principles of which consist of the purine derivatives defined above.

These reagents can be used as references or standards in studies of cell division.

Other characteristics and advantages of the invention are described in the examples which follow with reference to FIGS. 1 to 8, in which FIGS. 3 and 4 show respectively, the effects of roscovitine on maturation of ovocytes of the starfish and dephosphorylation of p34$^{cdc2}$ tyrosine in vivo, FIG. 7 shows the effects of roscovitine on the inhibition of the growth of L1210 cells and the halting of their cell cycle at G2/M, in FIG. 7A the growth of L1210 cells after exposure to various concentrations of roscovitine (mean ± standard deviation in relation to the growth of the untreated control cell) is shown, and in FIG. 7B the means (± standard deviation) of the distribution over the cycle of cells which have first been cultured for 48 hours in the presence or absence of 60 $\mu$M roscovitine are shown.

MATERIAL AND METHODS

Chemical products

Sodium orthovanadate, 1-methyladenine (1MeAde), EGTA, EDTA, MOPS, β-glycerophosphate, dithiothreitol (DTT), sodium fluoride, nitrophenyl phosphate, leupeptin, aprotinia, soya trypsin inhibitor, benzamidine, histone H1(type III-S), basic myelin protein, casein, protamine sulphate, isopropyl β-D-thiogalactopyranoside (IPTG), Sepharose 4B activated with CNBr, LB medium, glutethione and glutathione-Sepharose beads; all these products are such as those marketed by Sigma Chemicals.

The purine analogues are generally dissolved such that stock solutions of 100 mM in DMSO are available. The final concentration in DMSO in the reaction mixture is less than 1% (v/v).

[γ-$^{32}$P]-ATP is a product of Amersham.

The GST-retinoblastoma protein is expressed in bacteria and purified over glutathione-Sepharose beads as described previously in (1) and (2).

Buffers

Fiomogenization buffer:

60 mM β-glycerophosphate, 15 mM p-nitrophenyl phosphate, 25 mM MOPS (pH 7.2), 15 mM EGTA, 15 mM MgCl$_2$, 1 mM DTT, 1 mM sodium vanadate, 1 mM NaF, 1 mM phenyl phosphate, 10 $\mu$g leupeptin/ml, 10 $\mu$g aprotinin/ml, 10 $\mu$g soya trypsin inhibitor/ml and 100 $\mu$M benzadmidine.

Buffer C:

Composition of the homogenization buffer but with 5 mM EGTA, without NaF and without protease inhibitors.

Preparation of extracts of starfish ovocytes in phase M

To obtain preparations of ovoctye extracts on a large scale, the gonads of mature *Marthasterias glacialis* are removed and are incubated with 10 $\mu$M 1-MeAde in natural sea-water filtered over Millipore, until the eggs are laid. The ovecytes have thus all entered phase M. They are separated off from the incubation medium by centrifugation, frozen directly in liquid nitrogen and kept at −80° C. (see (1) and (3)).

The ovocytes in phase M are homogenized in the homogenization buffer in an amount of 2ml/g ovocytes.

After centrifugation for 45 minutes at 100,000 g, the supernatant is recovered and used directly for purification of the p34$^{cdc2}$/cyclin B kinase by affinity chromatography over p9$^{CKShs1}$ Sepharose beads (see (1) and (4)).

Enzymes

The activities of the kinases are determined at 30° C. in buffer C by means of counter-indication. The blank values are subtracted from the data and the activities are calculated in pmol of phosphate incorporated in the protein acceptor for an incubation of 10 minutes.

The controls are used with suitable dilutions in DMSO.

The phosphorylation of the substrate is determined, where appropriate, by autoradiography after SDS-PAGE.

p34$^{cdc2}$/cyclin B is purified from the phase M ovocytes of the starfish by affinity chromatography over p9$^{CKSml}$-Sepharose, where they are eluted with the aid of p9$^{CKSml}$ as described above (see (2), (3), and 5)).

For the determination, 1 mg histone H1 (Sigma type III-SV)/ml in the presence of 15 $\mu$M [γ-$^{32}$P]-ATP (3,000 Ci/mmol, 1 mCi/ml) in a final volume of 30 $\mu$l is used (see (1) and (6)).

After an incubation time of 10 minutes at 30° C., aliquots of 25 $\mu$l of supernatant are deposited on Whatman P81 phosphocellulose paper and, after 20 seconds, the filters are washed 5 times (for at least 5 minutes each time) in a solution of 10 ml phosphoric acid per liter of water.

The damp filters are transferred to 6 ml plastic scintillation ampoules, 5 ml SCS scintillation liquid (Amersham) are then added and the radioactivity is measured in a Packard counter.

The kinase activity is expressed in pmol of phosphate incorporated into histone H1 for an incubation of 10 minutes or in per cent of the maximum activity.

To carry out the kinetic experiments under linear conditions, the test system up to the final point for the p34$^{cdz2}$ kinase is used, as described, but, on the basis of preliminary tests, suitable unsaturated concentrations of substrate are used.

The p34$^{cda2}$/cyclin B kinase is added to obtain a linear activity with respect to the concentration of enzyme and to time.

In the majority of cases, this requires a 3- to 10-fold enzymatic dilution in buffer C.

The rate data are expressed in pmol incorporated into the substrate per second per amount of enzyme added. The apparent inhibition constants are determined by analysis by graph.

p33$^{cdc2}$/cyclin A and p33$^{cdk2}$/cyclin E are reconstituted from extracts of sf9 insect cells infected with various baculoviruses.

Cyclins A and B are fusion proteins of GST-cyclins and the complexes are purified over glutathione-Sepharose beads.

The kinase activities are determined with 1 mg/ml histone H1 (Sigma, type IIIS) in the presence of 15 $\mu$M [γ-$^{32}$p]-ATP for 10 minutes in a final volume of 30 $\mu$l, as described for the p34$^{cdc2}$/cyclin B kinase.

p33$^{cdk3}$/p25 is purified from the bovine brain (7), but the Mono S chromatography stage is not used.

The active fractions recovered from the Superose 12 column are combined and concentrated to a final concentration of about 25 $\mu$g enzyme/ml.

The determination of the kinase is carried out with 1 mg/ml histone H1 (Sigma, type IIIS) in the presence of 15 µM [y-$^{32}$P]-ATP over 10 minutes in a final volume of 30 µl, as described for p34$^{cdc2}$/cyclin B.

p33$^{cdk4}$/cyclin D1 is obtained from lysates of insect cells. cdk4 is a GST-cdk4 construction product and the active complex is purified over glutathione-Sepharose beads.

Its kinase activity is determined with a purified GST-retinoblastoma protein in the presence of 15 µM [y-$^{32}$P]-ATP in a final volume of 30 µl.

After incubation for 15 minutes, Laemmli buffer (2×30 µl) is added.

The phosphorylated substrate is resolved by 10% SDS-PAGE and analysed by autoradiography by exposure to MP Hyperfilm for about 14 hours and densitometry.

p33$^{cdk6}$/cyclin D2 is obtained from lysates of insect cells 8). For the tests, the procedure is as indicated above for the p33$^{cdk4}$/cyclin D1 protein.

The MAP kinases: GST-erk1 (9) cloned from a human HepG2 bank is expressed in bacteria, purified over glutathione-Sepharose beads and tested with 1 mg basic myelin protein per ml in the presence of 15 µM [y-$^{32}$P]-ATP as described above for the p34$^{cdc2}$/cyclin B kinase.

The erk1 and erk2 proteins marked with the aid of histone are activated in vitro by MAPKK, purified (affinity-Ni and Mono Q) and tested as described above for 10 minutes in a final volume of 20 µl.

The catalytic sub-unit of the cAMP-dependent kinase, purified from the bovine heart, is tested with 1 mg histone H1 per ml in the presence of 15 µM [y-$^{32}$P]-ATP as described above for p34$^{cdc2}$/cyclin B.

The cGMP-dependent kinase (10), purified to homogeneity from the smooth muscle of the trachea of bovine origin, is tested with 1 mg histone H1 per ml in the presence of 15 µM [y-$^{32}$P]-ATP as described above for p34$^{cdc2}$/cyclin B.

The casein 2 kinase is isolated from cytosol of the liver of the rat (11) and tested with 1 mg casein per ml and 15 µM [y-$^{32}$P]-ATP. The substrate is deposited on Whatman 3MM filters and washed with 10% TCA (w/v).

The short-chain myosin kinase purified from chicken gizzards (12) is tested in the presence of 100 nM calmodulin, 100 µM CaCl$_2$, 50 mM HEPES, 5 mM MgCl$_2$, 1 mM DTT and 0.1 mg BSA/ml at pH 7.5 using a synthetic peptide on the basis of the phosphorylation site of the light chain of myosin of the smooth muscle (KKRPQRATSNVFAM, 50 µM) and in the presence of 15 µM [y-$^{32}$P]-ATP in a final volume of 50 µl.

The incorporation of radioactive phosphate is checked on phosphocellulose filters as described above.

The homologous ASK-y in the GSK-3 plant is expressed as GST fusion protein in *E. coli* (13) and purified over glutathione-Sepharose. The activity of the ASK-y kinase is determined, over 10 minutes at 30° C., with 5 µgm basic myelin protein in the presence of 15 µM [y-$^{32}$P]-ATP in a final volume of 30 µl. The basic phosphorylated myelin protein is recovered on Whatman P81 phosphocellulose paper as described above for p34$^{cdc2}$/cyclin B.

The kinasic tyrosine domain for the insulin receptor (14) is over-expressed in a baculovirus system and purified to homogeneity. Its kinase activity is determined over 10 minutes at 30° C. with 5 µg Raytide (Oncogene Sciences) in the presence of 15 µM [y-$^{32}$P]-ATP in a final volume of 30 µl. The phosphorylated Raytide product is recovered on Whatman P81 phosphocellulose paper as described above for p34$^{cdc2}$/cyclin B.

Example 1: Synthesis of roscovitine

The synthesis is carried out in 3 stages and comprises the preparation 1) first of 6-benzylamino-2-chloropurine, then 2) of 6-benzylamino-2-chloro-9-isopropylpurine, and 3) of 6-benzylamino-2-R-(1-ethyl-2-hydroxyethylamino)-9-isopropylpurine.

1) Synthesis of 6-benzylamino-2-chloropurine:

The procedure is as described by Hocart in Phytochemistry 1991, 30, 2477–2486.

2) Synthesis of 6-benzylamino-2-chloro-9-isopropylpurine (I):

A mixture of 6-benzylamino-2-chloropurine (3.7 g; 14.2 mmol), potassium carbonate (11 g; 8 mmol) and isopropyl bromide 8.2 ml; 87 mmol) in 100 ml absolute DMSO is stirred at room temperature for three days. The absence of 6-benzylamino-2-chloropurine is confirmed by thin layer chromatography [CHCl$_3$-MeOH (98:2)]. The DMSO and the excess isopropyl bromide are removed by distillation in vacuo at below 50° C. The residue is partitioned between water and ethyl acetate. The organic phase is dried over Na$_2$SO$_4$ and evaporated in vacuo.

Crystallization in MeOH gives 3.51 g (82%) of product; m.p. 181–182° C., UV (MeOH): $\lambda_{uax4}$ 273.5, IR (Nicolet 205, KBr, DRIFT cm 1713, 1626, 1572, 1537, 1497, 1471, 1456, 1425, 1398, 1355, 1314, 1292, 1255, 1228, 1202.

3) Synthesis of 6-benzylamino-2-R-(1-ethyl-2-hydroxyethylamino)-9-isopropylpurine (II), racemic derivative:

A sealed ampoule, in which a vacuum has been established, containing 2.7 g (8.95 mmol) I and 17 ml (0.18 mol) R(-)-2-amino-1-butanol (Fluka 90%, R,S>9:1) is heated in an oven at 160–165° C. for 3 h 30 min. The excess amine is evaporated off at a temperature below 50° C. and the produce II is purified over a chromatography column using increasing amounts of MeOH in CHCl$_3$, that is to say 0, then 2, and 3%.

Crystallization in ethyl acetate gives 2.2 g II (69%), m. p. 132–134° C., [α]=+35.1 (c=0.29, CHCl). Mass spectrometry (Finnigam MAT 90, BE geometry 70 eV, temperature of the source 250° C., emission current 1 mA, acceleration voltage 5 keV, direct entry, DIP temperature between 190–220° C.]. HRMS was carried out by the method of overlapping peaks using Ultramark 1600 F. (PCR Inc., Fla. USA) as the standard] 354.2167 (M$^{+, C}_{19}$H$_{26}$N$_6$O Calc. 354.2168, 27%), 325 (7%), 324 (29%), 232 (100%), 295 (3%), 282 (7%), 281 (3%), 217 (6%), 185 (5%) 134 (3%), 91 (34%). FTIR (Nicolet 205, KEr, DRIFT. cm$^{-1}$): 1622, 1610, 1547, 1540, 1452, 1389, 1370, 1261, 1068.

Example 2: Study of the inhibitory properties on kinases of roscovitine and its effects on the cell cycle a) Study of the inhibitory properties on kinases The enzyme activities shown in the following table were measured after addition of roscovitine or olomoucine at increasing concentrations. These activities were measured with suitable substrates (histone H1, basic myelin protein, casein etc. . . ) with 15µM ATP.

The IC$_{50}$ were calculated from the dose/response curves obtained. The symbol (-) indicates that no inhibitory effect was observed. The highest concentration tested is given in parentheses.

TABLE 2

| Enzyme | IC$_{50}$ ($\mu$M) Roscovitine | Olomoutine |
|---|---|---|
| cdc2/cyclin B | 0.65 | 7 |
| cdc2/cyclin A | 0.7 | 7 |
| cdc2/cyclin E | 0.7 | 7 |
| cdc4/cyclin D1 | >1000 | >1000 |
| cdk5/P35 | 0.16 | 3 |
| cdk5/cyclin D3 | >500 | >250 |
| GST-erk1 | 30 | 30 |
| erk1 | 34 | 50 |
| erk2 | 14 | 40 |
| cAMP-dependent PK | >1000 | >2000 |
| cGMP-dependent PK | −(1000) | >2000 |
| Light chain myosin kinase | 90 | >1000 |
| Casein 2 kinase | −(1000) | >2000 |
| ASK-γ (GSK-3 plant) | 220 | 130 |
| Insulin receptor tyrosine kinase | 70 | 4000 |
| c-src | 250 | — |
| v-abl | >1000 | — |

Inhibition of cdc2, cdk2 and cdk5.

Examination of these results shows that roscovitine has an activity which is 10 times higher than olomoucine with respect to the targets cdc2 and cdk2 and 20 times higher with respect to cdk5.

By comparison, its effect seems limited, as observed with olomoucine, on the cdk4/cyclin D1 and cdk6/cyclin D2 kinases (the IC$_{50}$ are greater than 100 $\mu$M). This absence of an effect was confirmed with cdk4 originating from various sources. Working under identical conditions. GST-p16$^{INK4A}$ inhibits cdk4/cyclin D1.

Specificity of the inhibitory effect

As can be seen, the majority of the kinases are inhibited weakly or not at all.

Although roscovitine has an efficacy at least 10 times greater than that of olomoucine with respect to its cdk targets, its inhibitory effect is very similar to that of olomoucine with respect of erk1 and erk2. A 40-fold higher concentration of roscovitine thus seems necessary to inhibit erk1 (20-fold for erk2) in a manner similar to the inhibition of edc2.

b) Effect on ATP

To study the action mechanism of roseovitine, kinetic experiments were carried out in the presence of increasing concentrations of roscovitine varying the levels of ATP (from 0.1 to 0.5 mM), the concentration of histone H1 being kept constant at 0.7 mg/ml.

Figure 1:
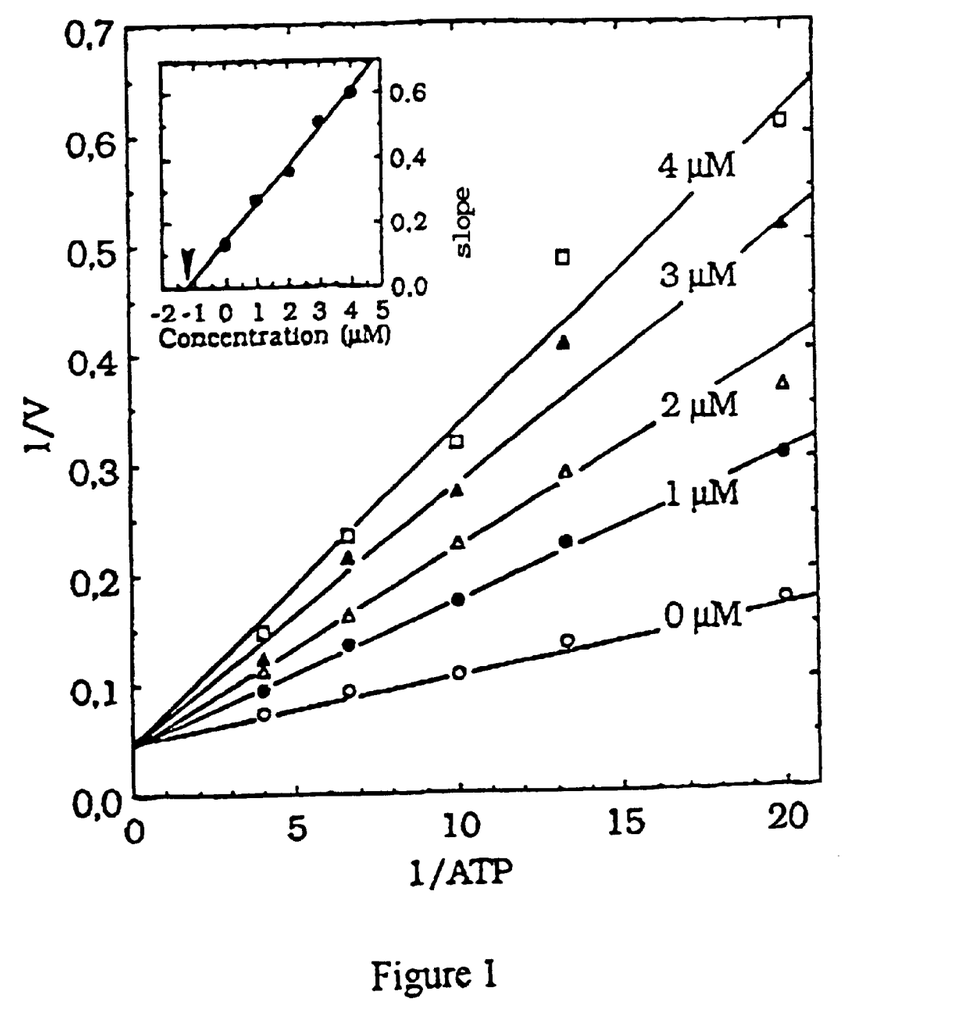
FIG. 1 shows the results of kinetics under linear conditions from tests relating to the activity of $p34^{cdc2}$/cyclin B at various concentrations of roscovitine.

The results are shown on FIG. 1.

These results demonstrate that roscovitine acts as a competitive inhibitor for ATP. Taking account of the linearity of the slopes as a function of the concentrations of roscovitine, it is called a linear inhibitor. The apparent inhibition constant Ki is 1.2 $\mu$M.

Analysis of the structure of the co-crystal of roscovitine and cdk2 confirms that, like olomoucine, roscovitine bonds to ATP in the bonding pocket and that its purine ring is orientated in the same way as that of olomoucine, that is to say in a totally different manner to the purine ring of ATP.

c) Study of the effect on the synthesis of DNA and the MPF activity.

The results of experiments carried out on several cell types are described.

Effect on the maturation of ovocytes of the starfish and on the dephosphorylation of p34$^{cdc2}$ tyrosine in vivo.

Figure 2:
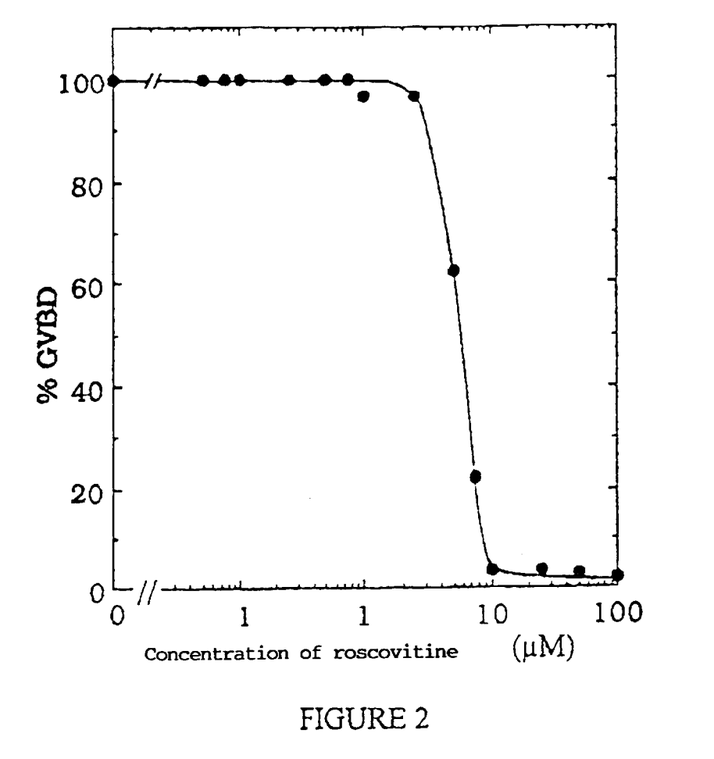
FIG. 2 shows the percentage breakdown of the germinal vesicle of ovocytes of the starfish as a function of the concentration of roscovitine.

The ovocytes of starfish, stopped at the prophase, are treated for 15 minutes with increasing concentrations of roscovitine before addition of the hormone 1-MeAde (1 $\mu$M). After 30 minutes, the % breakdown of the germinal vesicle (GVBD) is recorded. These values are shown on FIG. 2 as a function of the concentration of roscovitine (in $\mu$M). Roscovitine inhibits breakdown on the nuclear envelope with an IC$_{50}$ of 5 $\mu$M (the IC$_{50}$ of olomoucine working under the same conditions, is 30 $\mu$M). These results are given on FIG. 2.

As already observed with olomoucine, roscovitine reduces, but does not inhibit, the dephosphorylation of p34$^{cdc2}$ tyrosine in vivo. The ovocytes are treated with 10 $\mu$M roscovitine for 15 minutes before addition of 1 $\mu$M 1-MeAde at time 0. The extracts are prepared at various times and introduced on to a column of p9cksns1-Sepharose beads.

Figure 3:
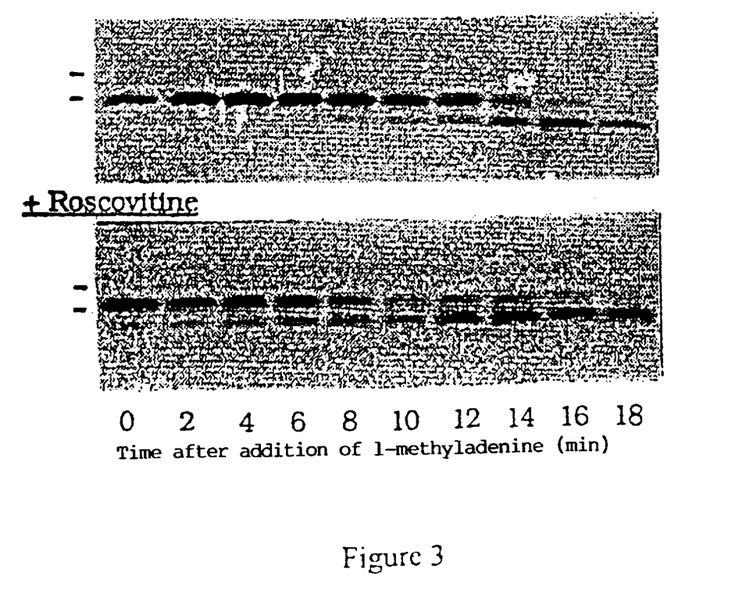

The proteins bonded to the beads are resolved by SDS-PAGE before carrying out a western blot with anti-PSTAIRE antibodies. A photograph of the western blot is shown on FIG. 3. The phosphorylated forms of p34$^{cdc2}$ appear in the upper part and the dephosphorylated forms appear in the lower part.

Roscovitine therefore inhibits not the activation of cdc2 but its activity. The dephosphorylation of p34$^{cdc2}$ tyrosine is catalysed by cdc25 and normally precedes the activation of the cdc2 kinase at the G2/M transition. Furthermore, the cdc2 kinase phosphorylates and over-activates cdc25 phosphatase. Roscovitine has thus been able to cause interruption at the cdc2 kinase level, bringing about a reduction in the dephosphorylation.

Effects on the mitotic cycle of sea urchin embryos.

Figure 4:
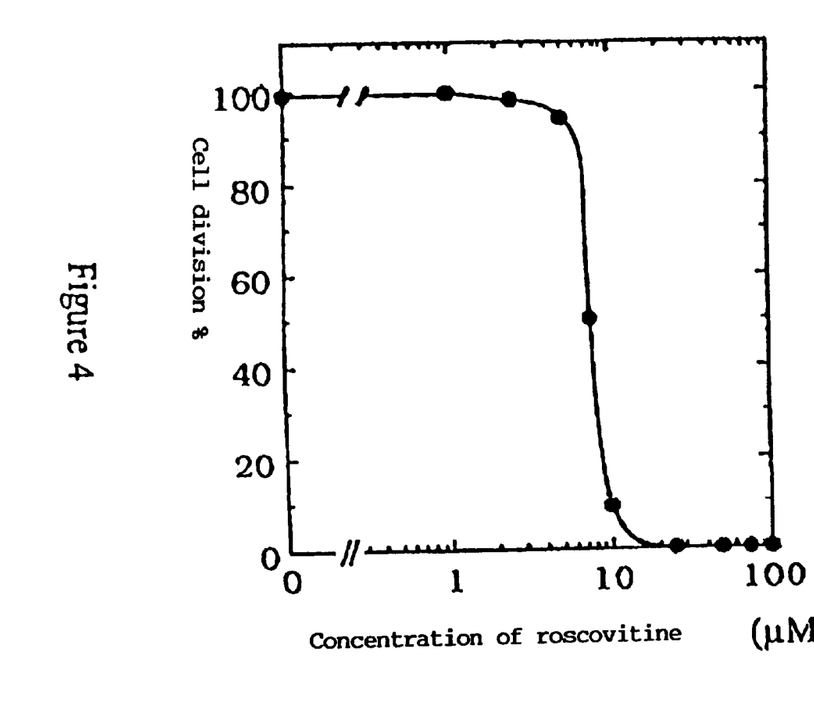
FIG. 4 shows the effects of roscovitine on the mitotic cycle of sea urchin embryos.

Roscovitine is added 60 minutes after fertilization. The percentage of embryos which have divided is recorded 120 minutes after fertilization. The results are given on FIG. 4.

It is found that is causes a dose-dependent halt at the late prophase stage.

The IC$_{50}$ is 10 $\mu$M. (Even at 100 $\mu$M, olomoucine causes only a slowing down of the prephase/metaphase transition, but does not stop the cells at the prophase).

Figure 5:
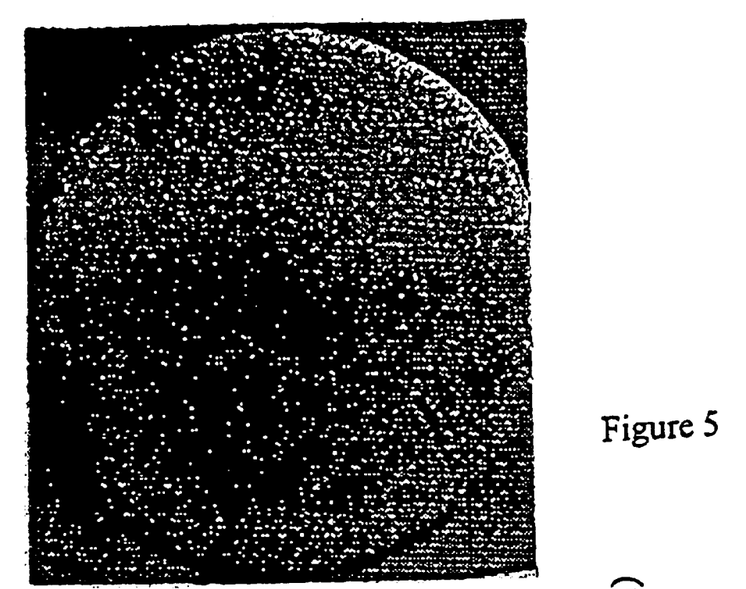
FIG. 5 shows these embryos stopped at the late prophase stage and FIG. 6 shows the effects of roscovitine on the synthesis of DNA in vitro and the MPF activity.

A large nucleus is observed in the eggs stopped in this way by roscovitine, as shown on FIG. 5.

This halt proves to be totally reversible. In fact, after several washing with sea-water, the eggs enter the mitotic cycles again and develop into normal pluteus larvae. These results are obtained even at elevated concentrations of roscovitine of 100 $\mu$M.

Effects on the synthesis of DNA in vitro and the MPF activity in extracts of Xenopus eggs.

The tests are carried out in accordance with (15), working as described in (1) for olomoucine.

The extracts of Xenopus stopped at the metaphase stage are incubated with roscovitine and sperm chromatin.

With concentrations of roscovitine ranging from 0 to 5 $\mu$M, the chromosomes remain highly condensed and no nuclear envelope is visible. At a concentration of 10 $\mu$M and above, interphase nuclei appear, with the chromatin partly decondensed and an intact nuclear envelope, showing that the MPF activity has been inhibited (the IC$_{50}$ is 5 $\mu$M).

The inhibition of DNA synthesis has also been studied, proceeding as described in (1) for olomoucine.

Roscovitine and sperm chromatin were thus added to an extract of eggs which had been stopped at the metaphase stage.

The extract was then abandoned at the interphase stage by addition of $CaCl_2$(15) and (16). The synthesis of total DNA was measured 3 h later by incorporation of [y-$^{32}$P]-dATP into material which can be precipitated with TCA.

Figure 6:
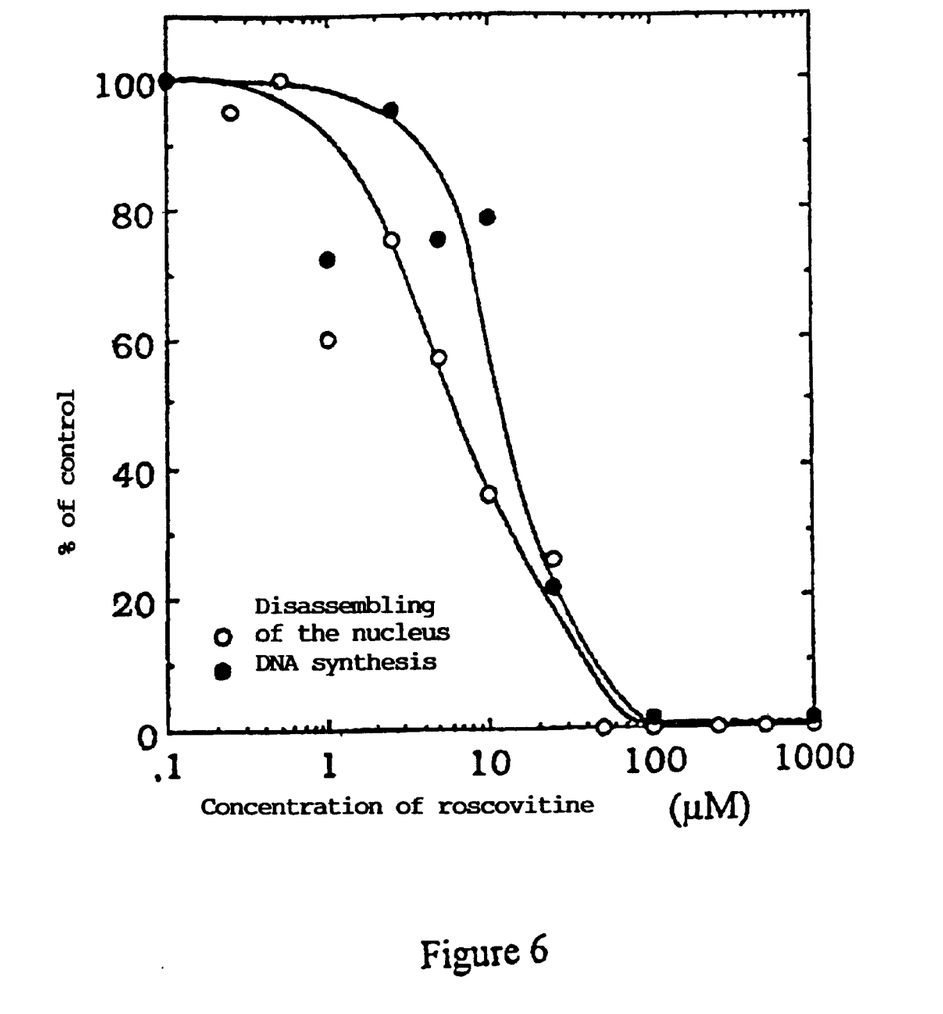

As shown in FIG. 6, the replication is inhibited by roscovitine with an $IC_{50}$ of 15 µM.

The invention thus provides new purines having inhibitory properties on cdc2/cyclin B of high specificity.

Example 3

Biochemical properties and effects of roscovitine on mammalian cells.

Method

In vitro screening of human tumoral cells

Sixty cell lines of human tumours comprising nine types of tumour were cultured for 24 hours prior to continuous exposure for 48 hours to 0.01–100 µM roscovitine. To estimate the cytotoxicity a sulphorhodamine B protein test was used.

Culture of the L1210 cell

L1210 cells sampled from cultures in exponential growth on RPMI-1640 medium supplemented with 10% foetal calf serum, penicillin and streptomycin were counted with the aid of a haemocytometer, placed in an amount of $5\times10^4$ cells per milliliter in 96-well tissue culture plates in the presence or in the absence of various concentrations of roscovitine or olomoucine, and then incubated at 37° C. under 5% $CO_2$. To reverse the effect of roscovitine, L1210 cells cultured for two days in the presence or absence of roscovitine were washed in PBS to remove any trace of active product, counted and placed again in fresh medium containing no active product (roscovitine or olomoucine). The cell growth was measured daily using the tetrazolium microculture test. The analysis of the cell cycle was carried out on cells fixed in ethanol, treated with 100 µg/ml RNase and stained with propidium iodide. Data acquisition was achieved with the aid of a Coulter flow cytometer (Hialeah, Fla., USA) EPICS Elite (registered trademark), and these data were analysed with the aid of Multicycle software (Phoenix Flow Systems, San Diego, Calif. USA) (registered trademark). All the tests were carried out with three repeats and all the experiments were repeated at least twice.

In vivo phosphorylation of vimentine

To study the in vivo phosphorylation of vimentine by the cdc2 kinase, the cells were either not treated or treated with 60 µM roscovitine for 48 hours prior to exposure to 10 ng/ml colcemide for an additional 2 hours. The cell extracts were then placed on a 10% SDS-PAGE gel for migration, transferred by western blots and incubated with 4A4 antibodies. These antibodies undergo a cross-reaction with vimentine phosphorylated by cdc2, but react neither with vimentine phosphorylated by other kinases (cAMP-dependent kinase protein, C kinase protein, $Ca^{2+}$-calmodulin-dependent kinase protein), nor with non-phosphorylated vimentine; the 4A4 antibodies specifically recognize vimentine which is phosphorylated at its Ser-55 residue by the cdc2 kinase when the cell enters mitosis.

Results

Roscovitine (0.01–100 µM; exposure for 48 hours) was tested on 60 human tumoral cell lines comprising nine types of tumours (leukaemia, cancer of larger cells of the lungs, cancer of the colon, cancer of the central nervous system, melanoma, cancer of the ovaries, cancer of the kidney, cancer of the prostate and cancer of the breast). All the cell lines had an equivalent sensitivity to roscovitine. The mean $IC_{50}$ value is 16 µM (whereas it is 60.3 µM for olomoucine). No correlation was found between the sensitivity of the cell lines to roscovitine and the presence of wild or muted p53. The method of comparison analysis showed that the effects of roscovitine and of flavopiridol are comparable.

Figure 7A:
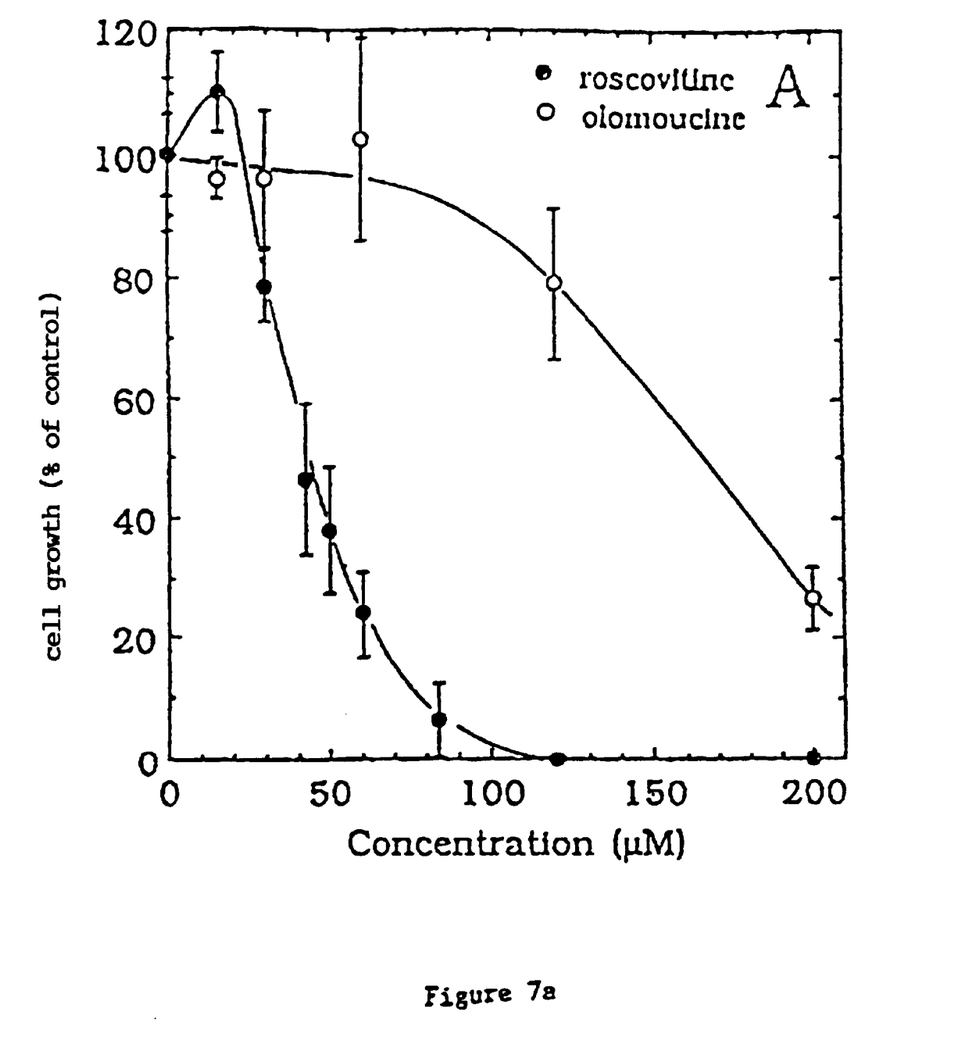
Figure 7B:
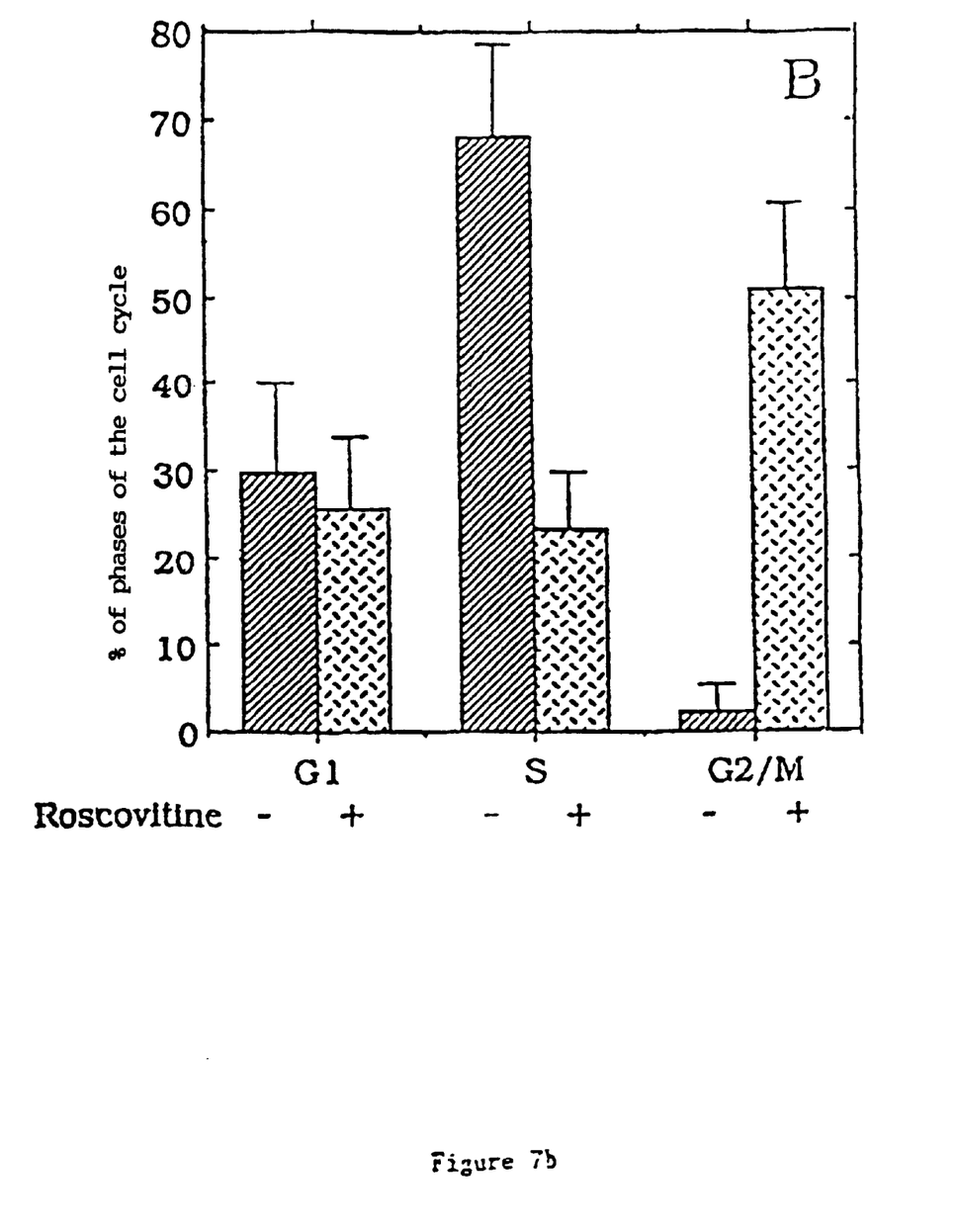

As regards the effects of roscovitine on the growth of the cell line L1210, a very clear dose-dependent inhibition of the growth was found, as shown on FIG. 7A, where the cell growth is shown as a function of the concentration of roscovitine or olomoucine. The curves are largely identical after two and three days of culture, as found with the abovementioned tumoral cells. Roscovitine is approximately four times more effective than olomoucine in inhibiting cell growth ($IC_{50}$ of 40 µM for roscovitine and 160 µM for olomoucine). Although the majority of cells are viable (96±2% by Trypan blue exclusion) after a treatment with 60 µM roscovitine for 48 hours, they remain irreversibly stopped, even after extensive washings. The cells exposed to 120 µM roscovitine die rapidly. The effects of roscovitine on the distribution of the cell cycle were then studied by flow cytometry. At 60 µM roscovitine, the cells remain stopped at G1 and accumulate in G2 as shown in FIG. 7B, where the proportions (%) of each phase of the cell cycle observed (G1, S, G2/M) in the presence or absence of roscovitine are shown.

Figure 8:
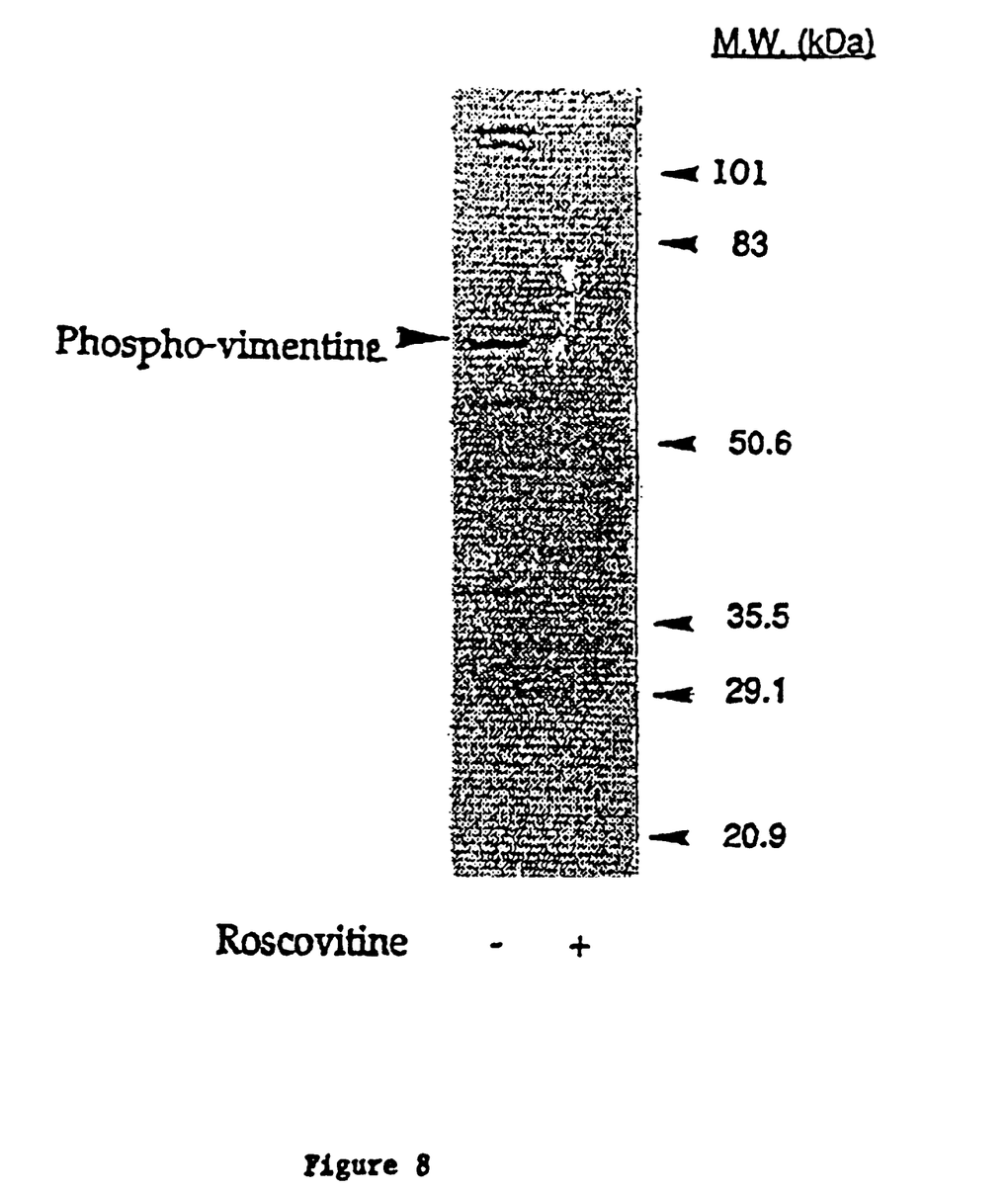
FIG. 8 shows the inhibitory effect of roscovitine on in vivo phosphorylation of vimentine at sites specific to cdc2.

4A4 antibodies were used with the aim of identifying the molecular target of roscovitine in vivo. The results are illustrated in FIG. 8, where the total proteins extracted from cells treated (+) or not treated (−) with roscovitine and then resolved on SDS-PAGE before western transfer with the 4A4 antibodies are shown. The non-treated cells stop in the metaphase and accumulate vimentine phosphorylated by cdc2. The cells treated with roscovitine on the other hand, do not have vimentine phosphorylated by cdc2, which shows that cdc2 has in fact been inhibited in vivo and that the cells were stopped before the metaphase.

Roscovitine also helps to reduce the hyperphosphorylation of tau observed during Alzheimer's disease: a cdk specific to the brain(cdk5/p35 ) which phosphorylates certain sites of tau is particularly sensitive to roscovitine.

BIBLIOGRAPHIC REFERENCES

1- Vesely et al. (1994) *Eur. J. Biochem.* 224, 771–786 II.

2- Azzi et al. (1994) *J. Biol. Chem.* 269, 13279–13288.

3- Baratte et al. (1992) *Anticancer Res.* 12, 873–880.

4- Azzi et al. (1992)*Eur. J. Biochem.* 203, 353–360.

5- Richardson et al. (1990) *Genes and Developments* 4, 1332–1554.

6- Meijer et al. (1991) *EMBO J.* 10, 1545–1344.

7- Lew et al. (1992) *J. Biol. Chem.* 267, 13383–13390.

8- Meyerson et al. (1994) *Molecul. Cellul. Biol.* 14, 2077–2086.

9- Charest et al. (1993) *Molecul. Cellul. Biol.* 13, 4679–4690.

10- Landgraf et al. (1989) *Eur. J. Biochem.* 181, 643–650.

11- Pinna, L. A. (1990) *Biochim. Biophys. Acta* 1054, 267–284.

12- Craig et al (1987) *J. Biol. Chem.* 262, 3278–3284.

13- Bianchi et al. (1994) *Mol. Gen. Genet.* 242, 337–345.

14- Kallen et al. (1990) *Biochem. Biophys. Res. Comm.* 168, 616–624.

15- Blow et al. (1986), *Cell* 47, 577–587.

16- Blow (1993) *J. Cell-Biol.* 122, 993–1002.

What is claimed is:

1. 2-(1-D,L-Hydroxymethylpropylamino)-6-benzylamino-9-isopropylpurine.

2. 6-benzylamino-2-R-(1-ethyl-2-hydroxyethylamino)-9-isopropyl purine.

3. A pharmaceutical composition comprising a therapeutically effective amount of the compound of claim 1 and a pharmaceutical vehicle.

4. A pharmaceutical composition comprising a therapeutically effective amount of the compound of claim 2 and a pharmaceutical vehicle.

* * * * *

UNITED STATES PATENT AND TRADEMARK OFFICE
CERTIFICATE OF CORRECTION

PATENT NO. : 6,316,456 B1  Page 1 of 1
DATED : November 13, 2001
INVENTOR(S) : Laurent Meijer et al.

It is certified that error appears in the above-identified patent and that said Letters Patent is hereby corrected as shown below:

<u>Title page,</u>
Item [73], the second Assignee's name should read as follows:
-- Institute of Experimental Botany, Academy of Science of the Czech Republic --.

Signed and Sealed this

Twenty-fourth Day of September, 2002

Attest:

Attesting Officer

JAMES E. ROGAN
*Director of the United States Patent and Trademark Office*

UNITED STATES PATENT AND TRADEMARK OFFICE
Certificate

Patent No. 6,316,456 B1                                         Patented: November 13, 2001

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Laurent Meijer, Roscoff, France; Emile Bisagni, Orsay, France; Michel Legraverend, Antony, France; and Miroslav Strnad, Olomouc, Czechoslavakia.

Signed and Sealed this Twenty-fourth Day of February 2004.

MUKUND SHAH
*Supervisory Patent Examiner*
Art Unit 1624